United States Patent

Golman et al.

[11] Patent Number: 5,716,598
[45] Date of Patent: Feb. 10, 1998

[54] A CONTRAST MEDIUM FOR MAGNETIC RESONANCE IMAGING USING PHYSIOLOGICALLY TOLERABLE MANGANESE COMPOUND

[75] Inventors: Klaes Golman, Rungsted Kyst, Denmark; Göran Pettersson, Hjärup, Sweden; Arne Berg, Blommenholm, Norway; Jo Klaveness, Oslo, Norway; Pál Rongved, Nesoddtangen, Norway; Peter Leander, Lund, Sweden

[73] Assignee: Nycomed Imaging AS, Oslo, Norway

[21] Appl. No.: 465,100

[22] Filed: Jun. 5, 1995

[30] Foreign Application Priority Data

Aug. 18, 1994 [GB] United Kingdom ............... 9416768

[51] Int. Cl.⁶ .................... A61K 49/00; A61B 5/055
[52] U.S. Cl. ............... 424/9.36; 424/9.3; 424/9.363; 424/9.361
[58] Field of Search ............... 424/9.3, 9.36, 424/9.361, 9.363; 128/653.4, 654

[56] References Cited

U.S. PATENT DOCUMENTS

| | | |
|---|---|---|
| 4,804,529 | 2/1989 | Bardy et al. . |
| 4,826,673 | 5/1989 | Dean et al. . |
| 4,859,451 | 8/1989 | Quay et al. . |
| 4,963,344 | 10/1990 | Gries et al. . |
| 5,128,121 | 7/1992 | Berg et al. . |
| 5,250,285 | 10/1993 | Lauffer et al. . |
| 5,290,537 | 3/1994 | Moore et al. . |
| 5,292,729 | 3/1994 | Ashmead . |
| 5,314,680 | 5/1994 | Rajagopalan et al. . |
| 5,439,668 | 8/1995 | Almen et al. . |

FOREIGN PATENT DOCUMENTS

| | | |
|---|---|---|
| 0 401 096 | 12/1990 | European Pat. Off. . |
| 0 524 633 | 1/1993 | European Pat. Off. . |
| 87/04622 | 8/1987 | WIPO . |
| 93/06811 | 4/1993 | WIPO . |

OTHER PUBLICATIONS

Johnson et al., *Proc. Soc. Exp. Biol. Med.*, 199(4), 470–480, 1992.

Seaborn et al., *Biol. Trace Elem. Res.*, 41(3), 279–294, Jun. 1994.

Bell et al., *J. Toxicol. Environ. Health*, 26(4), 387–398, 1989.

Giurgea et al., *Stud. Cercet. Biol. Scr. Biol. Anim.*, 44(2), 135–137, 1992.

Lonnerdal, *J. Nutr.*, 119(12), 1839–1844; discussion 1845, 1989.

Gerard et al., *Bull. Soc. Chim. Fr.*, No. 11–12, Pt. 1, 2404–2408, 1975.

Gerard, *Bull. Soc. Chim. Fr.*, No. 11–12, 451–456, 1979.

Rubin et al., *Magn. Reson. Med.*, 23(1), 154–165, 1992.

Stampfli et al., *J. Coord. Chem.*, 1(3), 173–177, 1972.

Petrola, *Finn. Chem. Lett.*, 13(5), 129–135, 1986.

*Primary Examiner*—Marvin M. Lateef
*Assistant Examiner*—Shawna J. Shaw
*Attorney, Agent, or Firm*—Bacon & Thomas

[57] ABSTRACT

There is provided a contrast medium composition for magnetic resonance imaging comprising a physiologically tolerable manganese compound, a physiologically tolerable reducing compound containing an α-hydroxy ketone group, or salt thereof and a physiologically tolerable carrier or excipient, having a manganese concentration of at least 0.3 mM or being in a dosage unit form containing at least 300 μmol manganese. Such compositions are particularly suitable for imaging of the liver.

8 Claims, 9 Drawing Sheets

A CONTRAST MEDIUM FOR MAGNETIC RESONANCE IMAGING USING PHYSIOLOGICALLY TOLERABLE MANGANESE COMPOUND

The present invention relates to improvements in and relating to magnetic resonance imaging (MRI) and in particular to compositions for use as or in the preparation of MRI contrast media for imaging of the liver, bile duct and gall bladder.

MRI is now well established as a medical diagnostic tool. The ability of the technique to generate high quality images and to differentiate between soft tissues without requiring the patient to be exposed to ionizing radiation has contributed to this success.

Although MRI can be performed without using added contrast media, it has been found that substances which affect the nuclear spin reequilibration of the nuclei (hereinafter the "imaging nuclei"—generally water protons in body fluids and tissues) responsible for the magnetic resonance (MR) signals from which the images are generated may be used to enhance image contrast and, accordingly, in recent years, many such materials have been suggested as MRI contrast agents.

The enhanced contrast obtained with the use of contrast agents enables particular organs or tissues to be visualized more clearly by increasing or by decreasing the signal level of the particular organ or tissue relative to that of its surroundings. Contrast agents raising the signal level of the target site relative to that of its surroundings are termed "positive" contrast agents whilst those lowering the signal level relative to surroundings are termed "negative" contrast agents.

The majority of materials now being proposed as MRI contrast media achieve a contrast effect because they contain paramagnetic, superparamagnetic or ferromagnetic species.

For ferromagnetic and superparamagnetic contrast agents, which are negative MRI contrast agents, the enhanced image contrast derives primarily from the reduction in the spin reequilibration parameter known as $T_2$ or as the spin-spin relaxation time, a reduction arising from the effect on the imaging nuclei of the fields generated by the ferromagnetic or superparamagnetic particles.

Paramagnetic contrast agents on the other hand may be either positive or negative MRI contrast agents. The effect of paramagnetic substances on magnetic resonance signal intensities is dependent on many factors, the most important of which are the concentration of the paramagnetic substance at the imaged site, the nature of the paramagnetic substance itself and the pulse sequence and magnetic field strength used in the imaging routine. Generally, however, paramagnetic contrast agents are positive MRI contrast agents at low concentrations where their $T_1$ lowering effect dominates and negative MRI contrast agents at higher concentrations where their $T_2$ lowering effect is dominant. In either event, the relaxation time reduction results from the effect on the imaging nuclei of the magnetic fields generated by the paramagnetic centres.

The use of paramagnetic, ferromagnetic and superparamagnetic materials as MRI contrast agents has been widely advocated and broad ranges of suitable materials have been suggested in the literature.

An example of a physiologically tolerable paramagnetic material known for use as an MRI contrast agent is manganese ion, which may conveniently be used in the form of its salts or chelates. Indeed, even at very low i.v. dosages (about 5–10 μmol/kg bodyweight) manganese has been found to be particularly effective as a contrast agent for imaging of the liver.

However manganese, when administered intravenously as a contrast agent, may be teratogenic at clinical dosages. Administered intravenously, manganese is also known to interfere with the normal functioning of the heart by replacement of calcium in the calcium pump of the heart.

In order to reduce the direct effect on the heart, oral administration has been proposed. This ensures passage of the contrast agent through the liver before going to the heart.

Oral administration of $MnCl_2$ as a liver imaging MR contrast agent has been proposed and orally administered $MnCl_2$ has not been found to be teratogenic. However, the absorption of $MnCl_2$ through the gut is poor, and as a result the dosage required for clinical efficacy is of the order of 200 μmol/kg bodyweight. In the event of damage to the gut resulting in increased uptake, such a high dosage level still has the potential for causing undesired adverse effects, eg. cardiac effects.

We have now surprisingly found that gastrointestinal tract manganese contrast agents suitable for imaging of the liver may be produced by the incorporation of a reducing compound containing an α-hydroxy ketone group (—C(OH)—CO—) as an uptake promoter.

Thus, viewed from one aspect the present invention provides a contrast medium composition comprising a physiologically tolerable manganese compound, a physiologically tolerable reducing compound containing an α-hydroxy ketone group, or salt thereof and a physiologically tolerable carrier or excipient, having a manganese concentration of at least 0.3 mM or being in a dosage unit form containing at least 300 μmol manganese.

The manganese compound, which preferably is soluble in gastrointestinal fluid may for example be a chelate or a salt. Particularly preferred are metal chelates and salts in which the manganese is present as Mn(II) rather than Mn(III) since the former has a higher magnetic moment and thus is more effective as an MR contrast agent.

The reducing nature of the uptake promoter is important since normal uptake of manganese by the gut tends to favour Mn(II) rather than Mn(III).

Preferred compositions according to the invention are those in which the reducing compound further contains an oxygen atom in a heterocyclic ring structure.

Particularly preferred as an uptake promoter in the compositions of the invention is ascorbic acid which has been found to increase the uptake of manganese in the liver by a factor of about 5 compared with oral administration of $MnCl_2$ alone. This surprising increase is demonstrated in the Figures of the accompanying drawings. Moreover ascorbic acid (vitamin C) is particularly preferred as an uptake promoter since it is cheap, readily available and particularly well tolerated by the body.

Yet more particularly preferred compositions in accordance with the invention are those in which the uptake promoter is kojic acid. The dramatic increase in the uptake of manganese in the liver following administration of $MnCl_2$+ kojic acid can be seen from FIG. 5 of the accompanying drawings.

Using the compositions of the invention, the liver can be effectively imaged with a significant reduction in the dosage of manganese required. Thus, for example, a 50% enhancement of the liver can be obtained by oral administration of 100 μmol manganese/kg body weight and 1 mmol/kg ascorbic acid. Such a dosage results in the same degree of enhancement of the liver as 5 μmol Mn(II)/kg body weight $MnCl_2$ (i.v.) or as 500 μmol Mn(II)/kg body weight $MnCl_2$ (p.o.).

FIG. 1 hereto demonstrates the effect of p.o. administration of $MnCl_2$ and ascorbic acid on liver enhancement compared with p.o. administration of $MnCl_2$ alone.

Increase in the ratio of ascorbic acid to $MnCl_2$ results in an increase in the enhancement effect obtained. This dose-response relationship can be seen from FIG. 2 hereto.

The gradual increase in enhancement of the liver with time following administration of a composition in accordance with the invention enables the dynamics of uptake of the contrast agent by the liver to be monitored (see for example FIG. 2). This is of particular importance in enabling identification of areas of healthy tissue and areas of possible tumor growth.

In the compositions according to the invention, the preferred molar ratio of manganese to uptake promoter is from 1:0.2 to 1:50, eg. 1:1 to 1:20, especially 1:3 to 1:6, particular preferably about 1:5.

The uptake promoter may if desired be present in whole or in part as the counterion to the manganese ions. Thus in one embodiment the composition of the invention comprises as both manganese compound and uptake promoter a manganese salt of a reducing compound containing an α-hydroxy ketone group, eg. manganese (II) ascorbate.

The compositions according to the invention may be used to achieve a so-called "double contrast effect" by increasing the signal level from the liver whilst at the same time decreasing that from the surrounding tissues, in particular from the gut. Such an effect enables yet further enhancement of the liver.

A double contrast effect can be achieved with the compositions of the invention since the resulting manganese ion concentration within the g.i. tract will generally be such as to create a signal suppressing effect there. In this case, to avoid image artefacts resulting from pockets of the gut being contrast agent free, it is desirable to incorporate in the compositions a viscosity enhancing agent and desirably also an osmoactive agent. Examples of suitable viscosity enhancers and osmoactive agents are described in WO 91/01147 and WO 91/01148.

When using the compositions of the invention to achieve this double contrast effect, it is particularly preferable to incorporate a viscosity enhancing agent which attains its full viscosity enhancing effect only after administration of the contrast medium. The contrast medium is thus able to be ingested in a relatively tolerable form while yet developing the desired viscosity at or during passage towards the site which is to be imaged.

The compositions of the invention are particularly suited to use, if required after dispersion in aqueous media, for imaging of the liver. For such a purpose the compositions may be administered into the gastrointestinal tract orally, rectally or via a stomach tube.

Thus, viewed from a further aspect the present invention provides a method of generating a magnetic resonance image of a human or non-human, preferably mammalian, animal body which method comprises administering into the gastrointestinal tract of a said body a contrast medium comprising a physiologically tolerable manganese compound and a physiologically tolerable reducing compound containing an α-hydroxy ketone group or salt thereof and generating a magnetic resonance image of the liver and abdomen of said body.

It is possible to formulate the contrast medium immediately or shortly prior to administration by mixing the reducing compound with the manganese species. Thus, in a further aspect the invention also provides an MRI contrast agent kit comprising in a first container a physiologically tolerable manganese compound, and in a second container a physiologically tolerable reducing compound containing an α-hydroxy ketone group, or salt thereof.

The contrast agent composition of the invention may of course include components other than the uptake promoter, the manganese compound, the viscosity enhancing and osmoactive agents, for example conventional pharmaceutical formulation aids such as wetting agents, buffers, disintegrants, binders, fillers, flavouring agents and liquid carrier media such as sterile water, water/ethanol etc.

For oral administration, the pH of the composition is preferably in the acid range, eg. 3 to 8 and while the reducing compound may itself serve to yield a composition with this pH, buffers or pH adjusting agents may be used.

The contrast media may be formulated in conventional pharmaceutical administration forms, such as tablets, capsules, powders, solutions, dispersions, syrups, suppositories etc.

The preferred dosage of the composition according to the present invention will vary according to a number of factors, such as the administration route, the age, weight and species of the subject and the particular uptake promoter used. Conveniently, the dosage of manganese will be in the range of from 5 to 150 μmol/kg bodyweight, preferably from 10 to 100 μmol/kg bodyweight, while the dosage of the uptake promoter will be in the range of from 5 μmol to 1 mmol/kg bodyweight, preferably from 25 μmol to 0.5 mmol/kg bodyweight.

Preferred embodiments of the invention will now be described by reference to the following non-limiting Examples and the accompanying drawings, in which.

Figure 1:
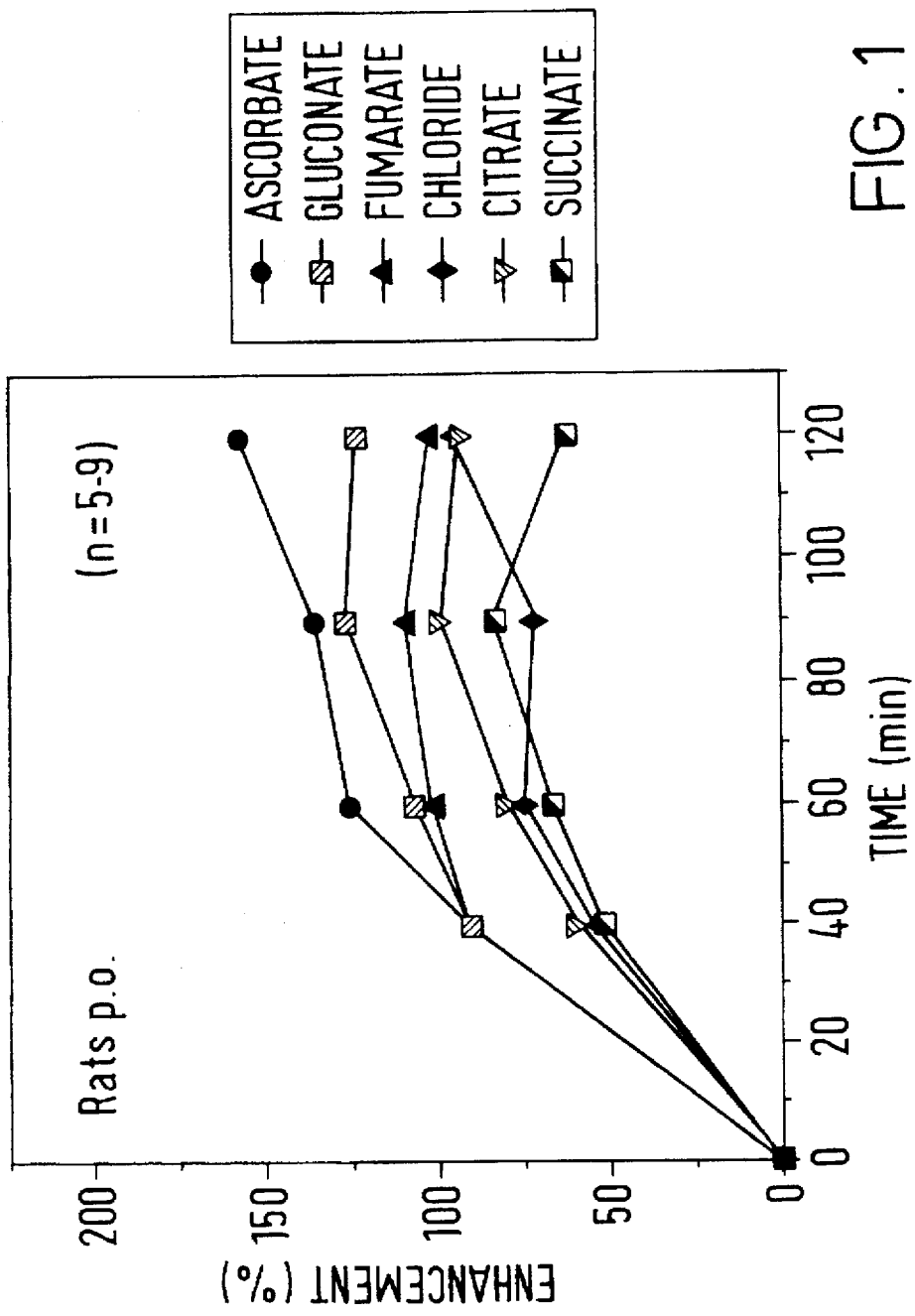
FIG. 1 is a graph illustrating the effect of p.o. administration of different $Mn^{2+}$ salts on liver enhancement.
Figure 2:
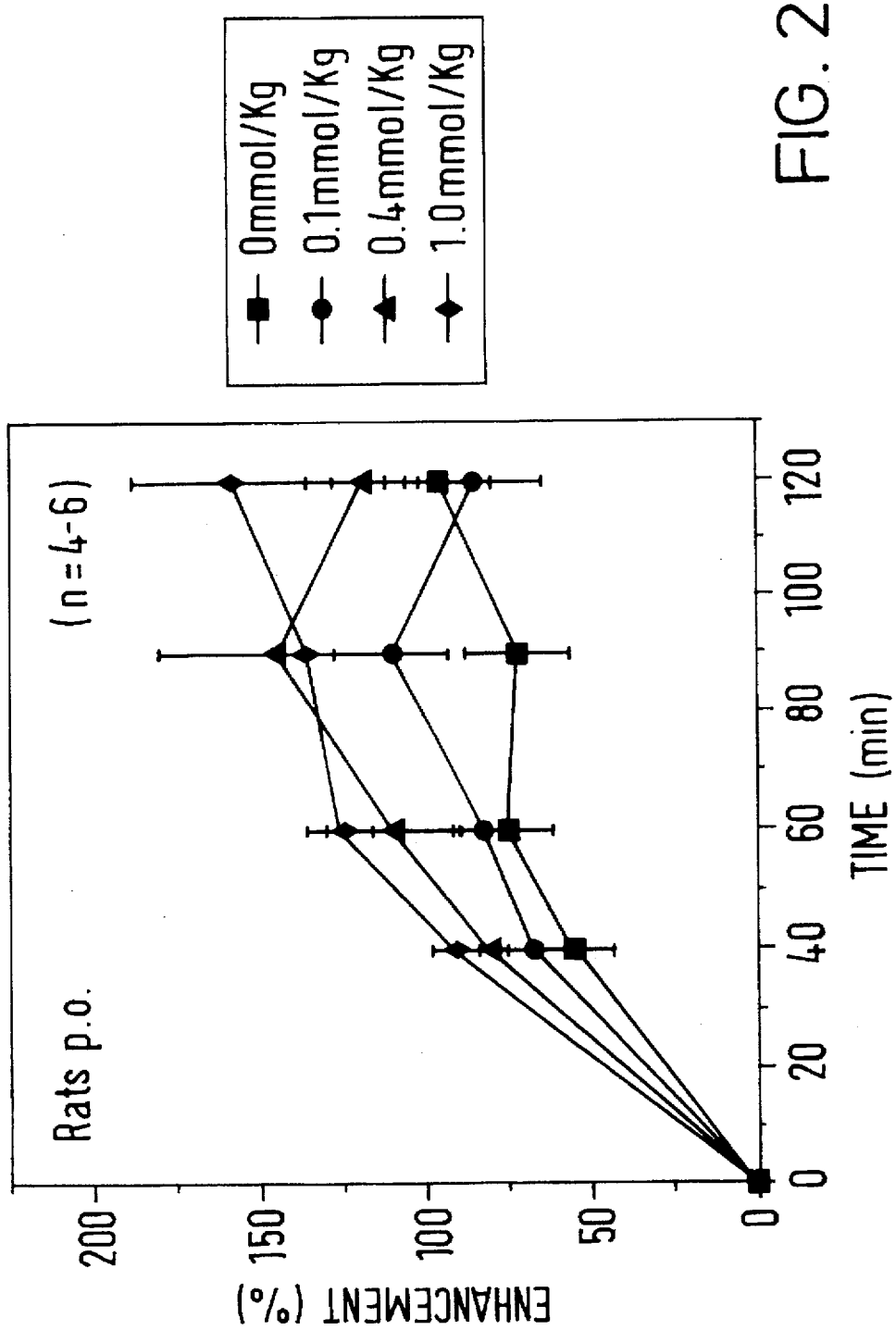
FIG. 2 is a graph illustrating the effect of p.o. administration of $MnCl_2$+ascorbic acid on liver enhancement at varying concentrations of ascorbic acid.
Figure 3:
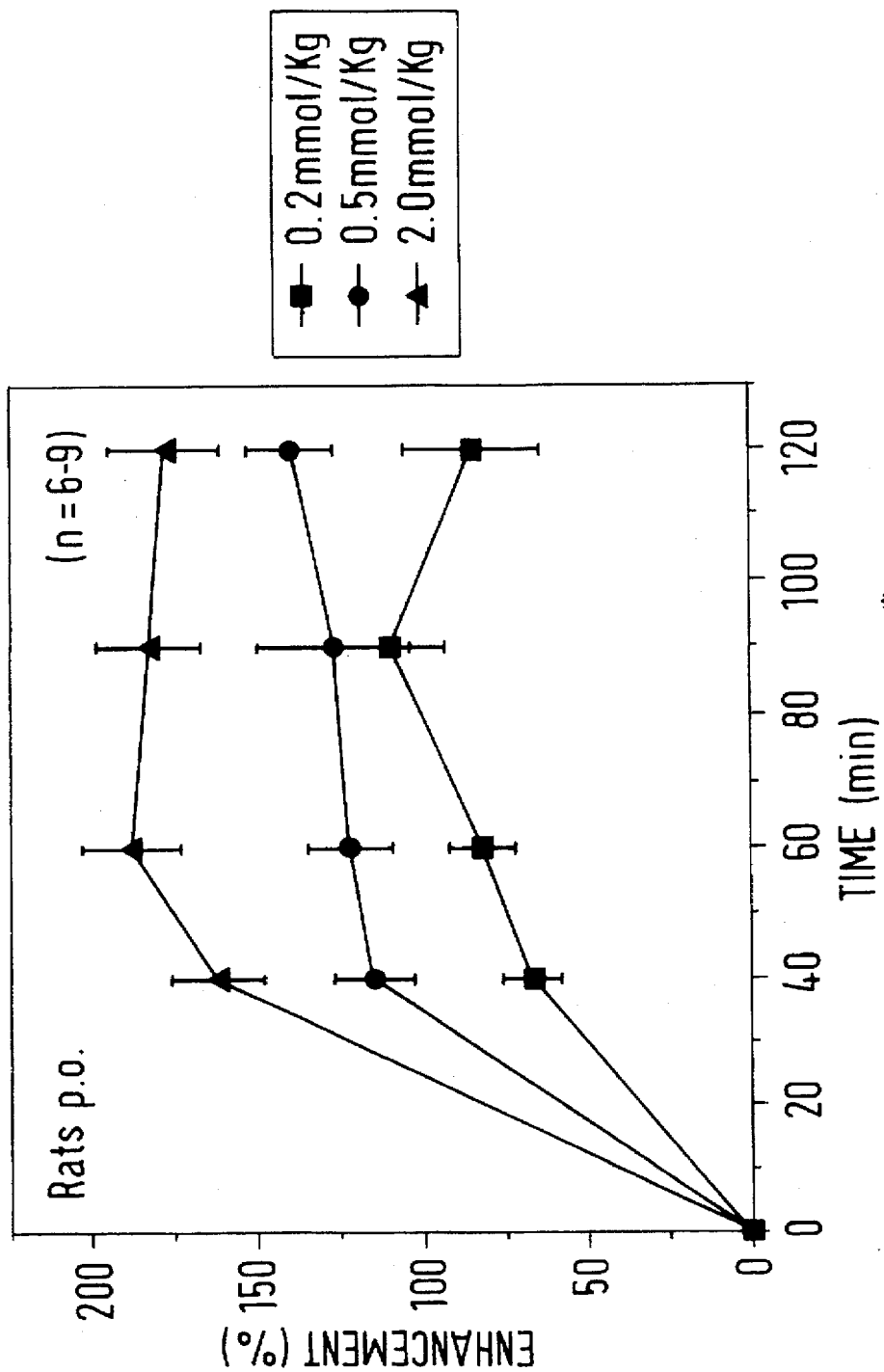
FIG. 3 is a graph illustrating the effect of administration of different doses of $MnCl_2$ containing 0.1 mmol/kg ascorbic acid on liver enhancement.
Figure 4:
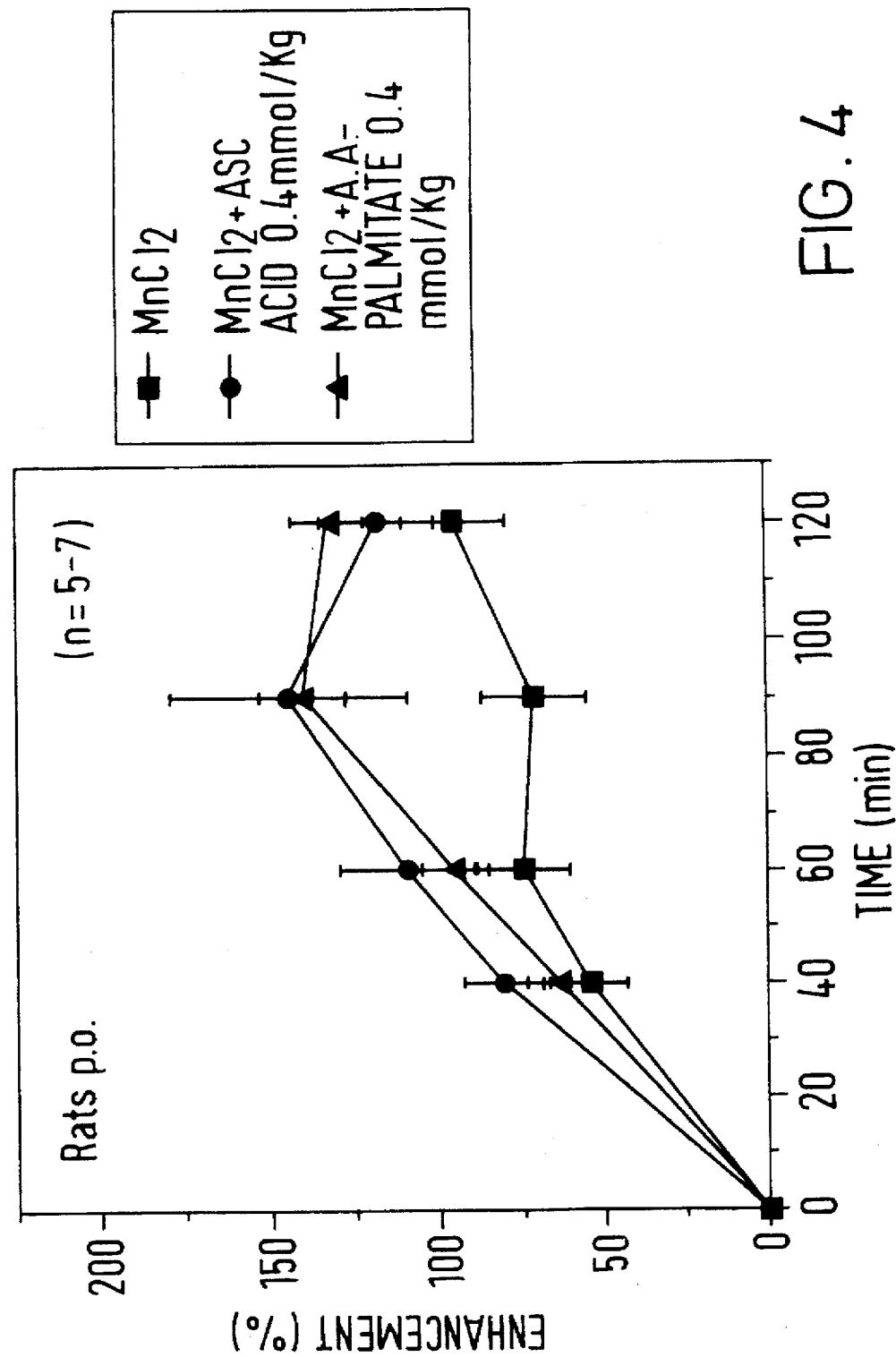
FIG. 4 is a graph illustrating the effect of the addition of ascorbic acid or ascorbic acid-palmitate to $MnCl_2$ on enhancement of the liver.
Figure 5:
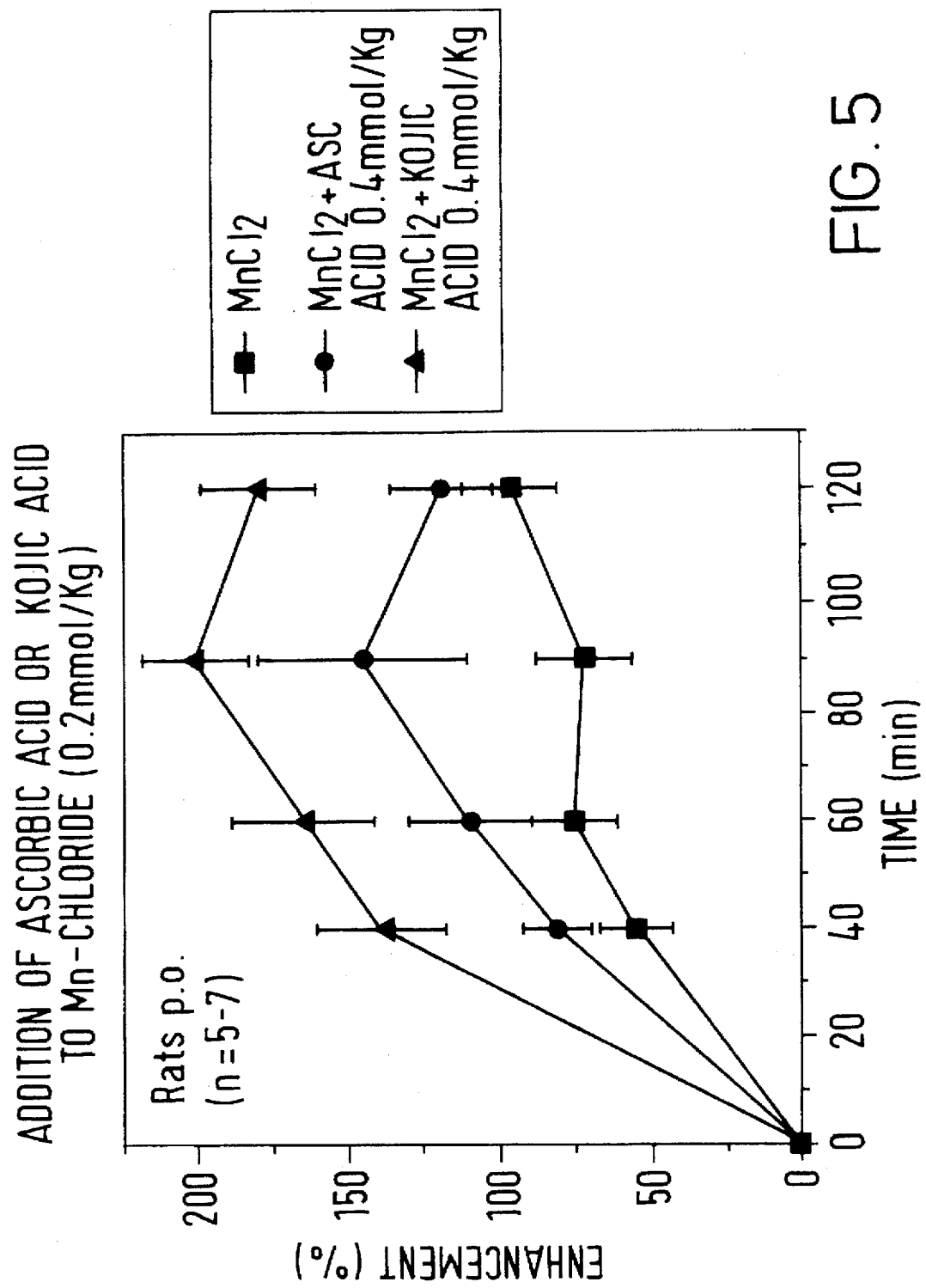
FIG. 5 is a graph illustrating the effect of the addition of ascorbic acid or kojic acid to $MnCl_2$ on enhancement of the liver.
Figure 6:
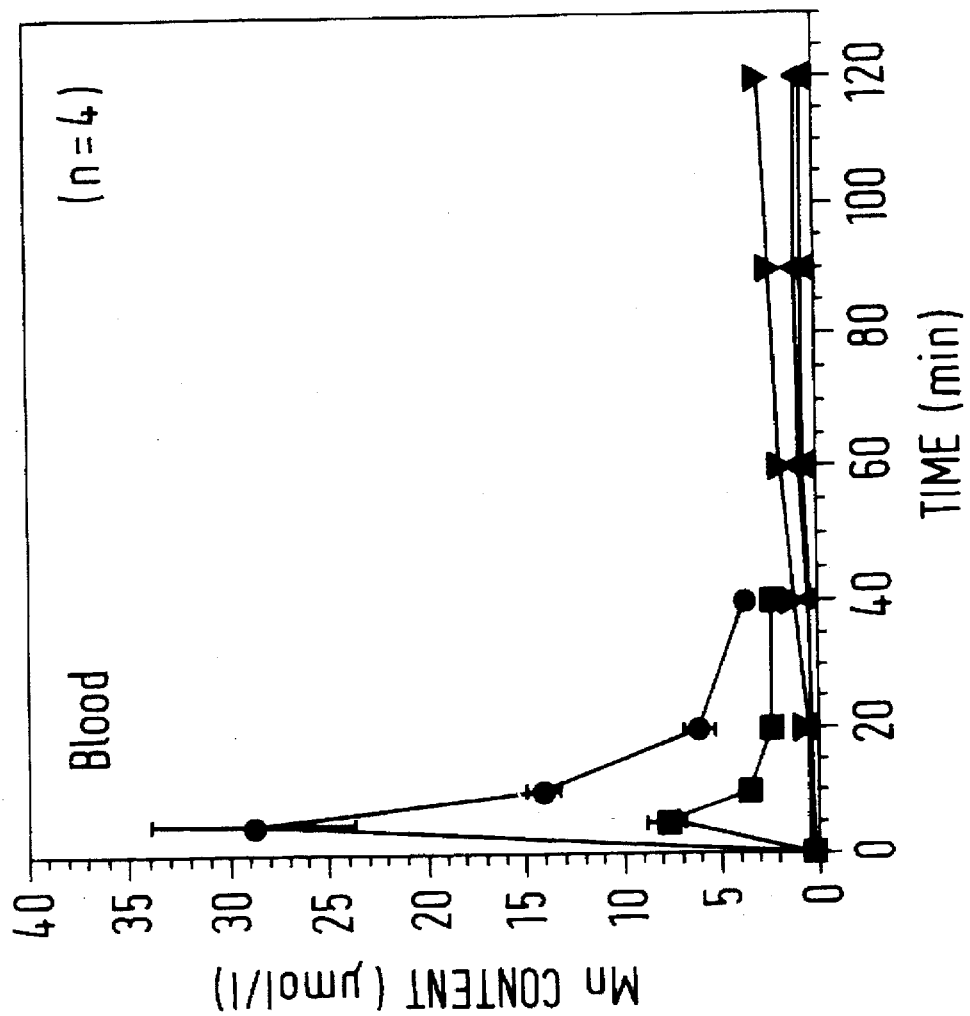
FIG. 6 is a graph illustrating the results of a pharmacokinetic study to determine the variation in concentration of Mn(II) in the blood following administration of various Mn(II)-containing compositions.
Figure 7:
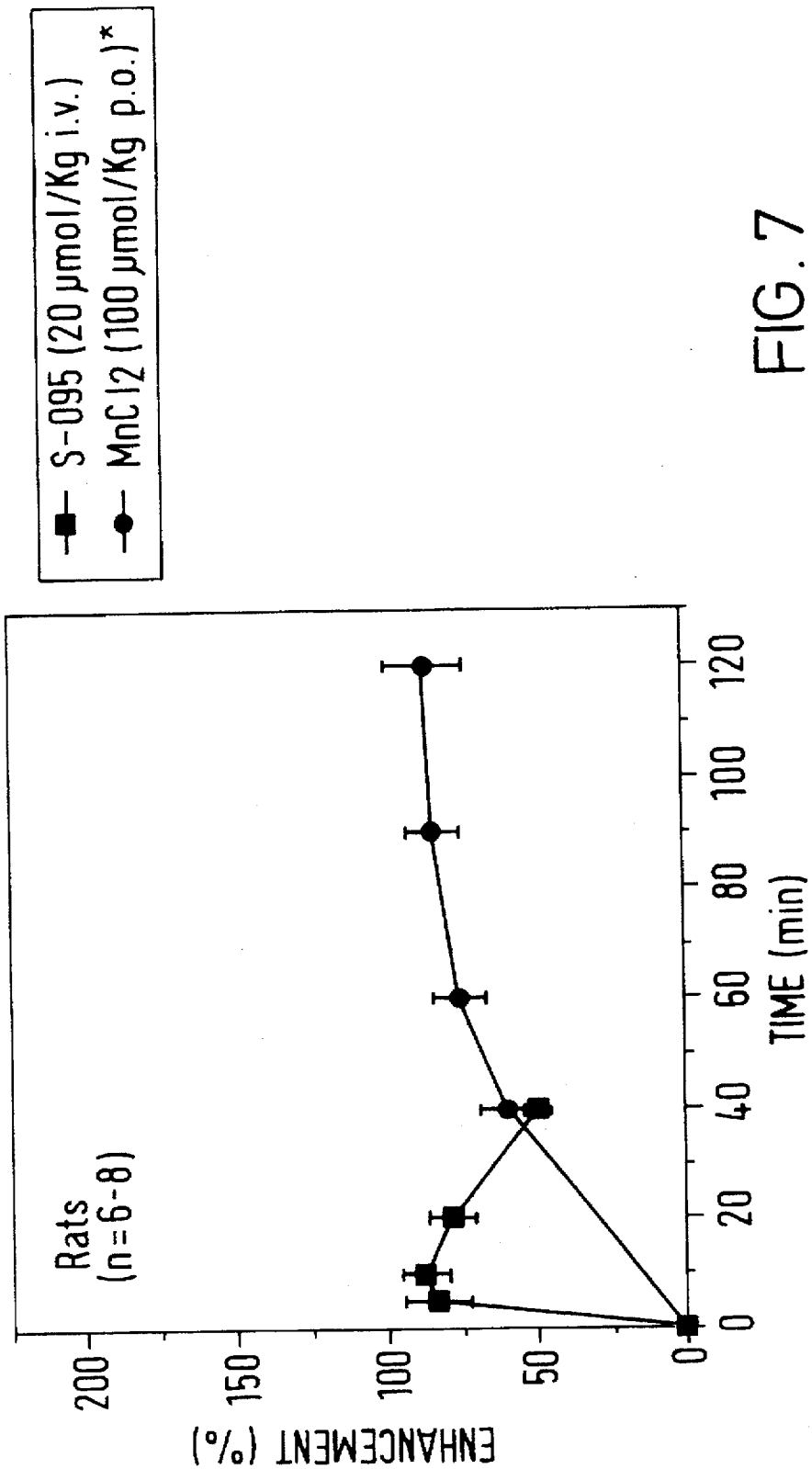
FIG. 7 is a graph comparing the effect on liver enhancement of i.v. administration of Mn DPDP (S-095) with that of p.o. administration of $MnCl_2$+ascorbic acid.
Figure 8:
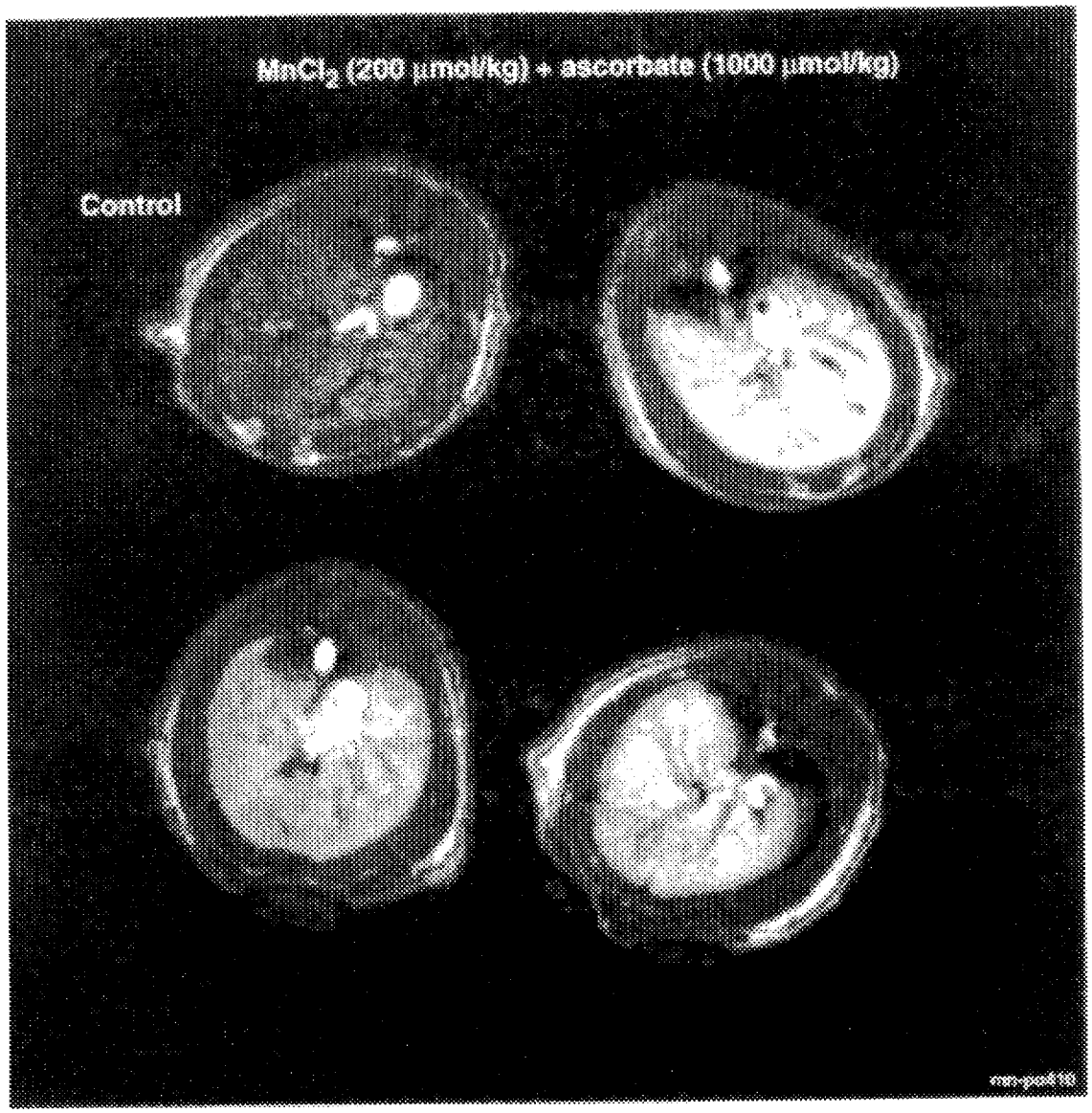
FIG. 8 illustrates transversal T1-weighted (SE 57/13; 2.4 T) liver images from a control rat and from three rats 2 hours after oral administration of 200 μmol/kg $MnCl_2$+1000 μmol/kg ascorbate. The signal intensity of the liver is substantially increased after garage administration of $Mn^{2+}$ and ascorbate.
Figure 9:
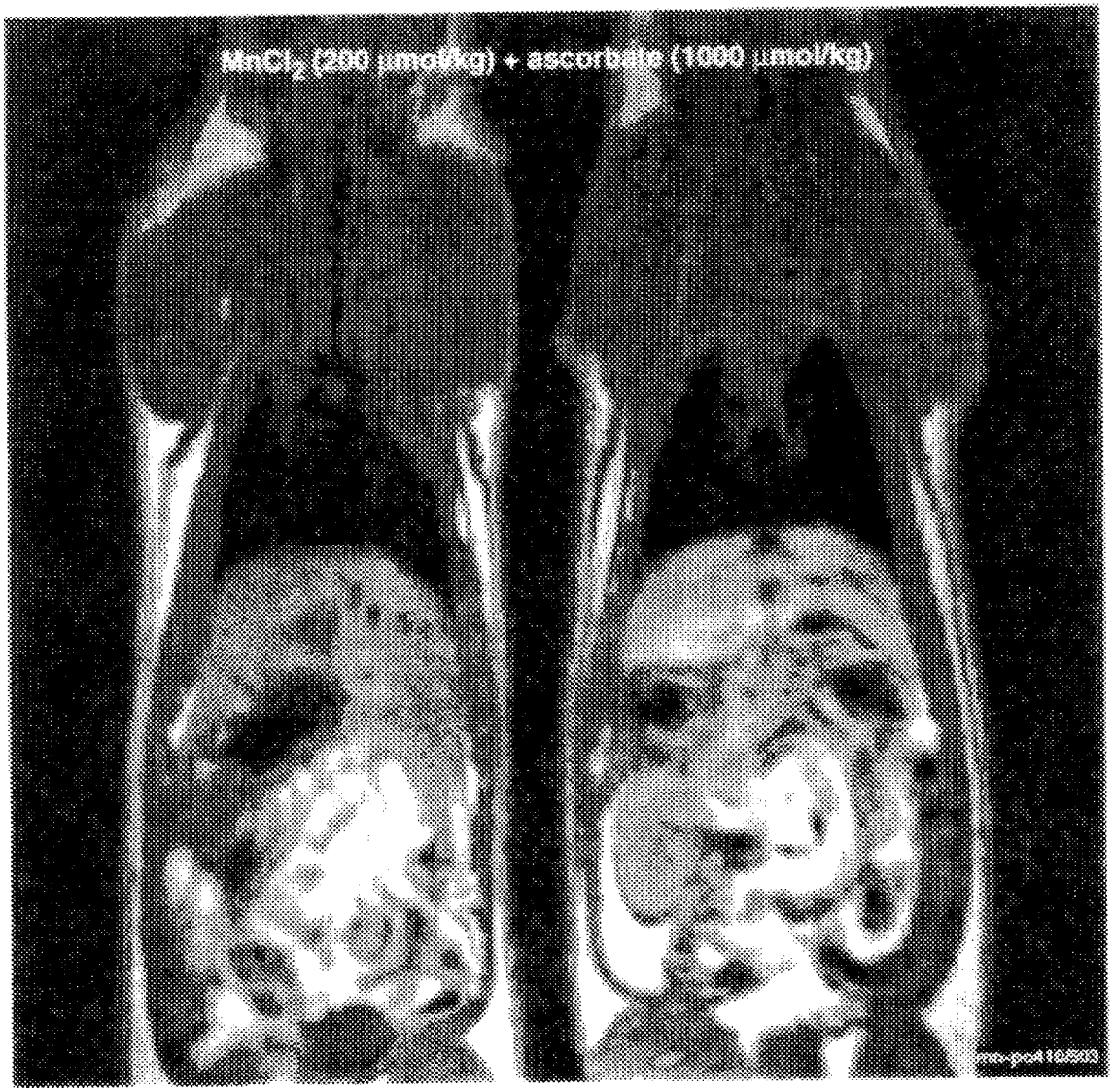
FIG. 9 illustrates coronal T1-weighted (SE 90/17; 2.4 T) liver images from two rats 2 hours after oral administration of 200 μmol/kg $MnCl_2$+1000 μmol/kg ascorbate. The signal intensity in the gastrointestinal lumen is reduced after administration of $Mn^{2+}$.

For the measurement of the curves of FIGS. 1 to 7 the following materials were used:

FIG. 1

| Mn-ascorbate | |
|---|---|
| MnCl$_2$ × 2H$_2$O | 6.48 g |
| Ascorbic acid | 35.2 g |
| Water ad | 1000 ml |
| Mn-gluconate | |
| Mn-gluconate | 19.2 g |
| Water ad | 1000 ml |
| Mn-citrate | |
| MnCl$_2$ × 2H$_2$O | 6.48 g |
| Na$_3$-citrate × 2H$_2$O | 23.5 g |
| Water ad | 1000 ml |

FIG. 2

| MnCl$_2$ | |
|---|---|
| MnCl$_2$ × 2H$_2$O | 6.48 g |
| Water ad | 1000 ml |
| MnCl$_2$ + 0.1 mmol/kg ascorbic acid | |
| MnCl$_2$ × 2H$_2$O | 6.48 g |
| Ascorbic acid | 3.52 g |
| Water ad | 1000 ml |
| MnCl$_2$ + 0.4 mmol/kg ascorbic acid | |
| MnCl$_2$ × 2H$_2$O | 6.48 g |
| Ascorbic acid | 14.1 g |
| Water ad | 1000 ml |
| MnCl$_2$ + 1.0 mmol/kg ascorbic acid | |
| MnCl$_2$ × 2H$_2$O | 6.48 g |
| Ascorbic acid | 35.2 g |
| Water ad | 1000 ml |

FIG. 3

| MnCl$_2$ (0.2 mmol/kg) + ascorbic acid | |
|---|---|
| MnCl$_2$ × 2H$_2$O | 6.48 g |
| Ascorbic acid | 3.52 g |
| Water ad | 1000 ml |
| MnCl$_2$ (0.5 mmol/kg) + ascorbic acid | |
| MnCl$_2$ × 2H$_2$O | 16.2 g |
| Ascorbic acid | 3.52 g |
| Water ad | 1000 ml |
| MnCl$_2$ (2.0 mmol/kg) + ascorbic acid | |
| MnCl$_2$ × 2H$_2$O | 64.8 g |
| Ascorbic acid | 3.52 g |
| Water ad | 1000 ml |

FIG. 4

| MnCl$_2$ | |
|---|---|
| MnCl$_2$ × 2H$_2$O | 13.0 g |
| Water ad | 1000 ml |
| MnCl$_2$ + ascorbic acid – palmitate (0.4 mmol/kg) | |
| L-ascorbic acid 6-palmitate | 66.4 g |
| Polyethylene glycol 300 ad | 1000 ml |

FIG. 5

| MnCl$_2$ + kojic acid (0.4 mmol/kg) | |
|---|---|
| MnCl$_2$ × 2H$_2$O | 6.48 g |
| Kojic acid | 11.4 g |
| Water ad | 1000 ml |

EXAMPLE 1

| Oral Composition | |
|---|---|
| MnCl$_2$ × 2H$_2$O | 6.48 g |
| Ascorbic acid | 35.2 g |
| Water ad | 1000 ml |

The manganese chloride and ascorbic acid are dissolved in sterile deionised water. The dose for a 70 kg adult human would be 350 ml, taken orally.

EXAMPLE 2

| Oral Composition | |
|---|---|
| MnCl$_2$ × 2H$_2$O | 6.48 g |
| Kojic acid | 11.4 g |
| Water ad | 1000 ml |

The manganese chloride and kojic acid are dissolved in sterile deionised water. The dose for a 70 kg adult human would be 350 ml, taken orally.

EXAMPLE 3

| Oral Composition | |
|---|---|
| A. | |
| MnCl$_2$ × 2H$_2$O | 13.0 g |
| Water ad | 1000 ml |
| B. | |
| L-ascorbic acid 6-palmitate | 66.4 g |
| Polyethylene glycol 300 ad | 1000 ml |

The dose for a 70 kg adult human would be 175 ml of A and 175 ml of B, taken orally.

We claim:

1. A contrast medium composition for magnetic resonance imaging comprising a physiologically tolerable manganese compound, an uptake promoter comprising a physiologically tolerable reducing compound containing an α-hydroxy ketone group, or salt thereof and a physiologically tolerable carrier or excipient, having a manganese concentration of at least 0.3 mM or being in a dosage unit form containing at least 200 µmol manganese and wherein the molar ratio of manganese to uptake promoter is from 1:0.2 to 1:50.

2. A composition as claimed in claim 1 wherein the manganese compound is a chelate or a salt in which the manganese is present as Mn(II).

3. A composition as claimed in claim 1 wherein the reducing compound further contains an oxygen atom in a heterocyclic ring structure.

4. A composition as claimed in claim 1 wherein the uptake promoter is ascorbic acid.

5. A composition as claimed in claim 1 wherein the uptake promoter is kojic acid.

6. A composition as claimed in claim 1 comprising as both manganese compound and uptake promoter a manganese salt of a reducing compound containing an α-hydroxy ketone group.

7. A method of generating a magnetic resonance image of a human or non-human animal body which method comprises administering into the gastrointestinal tract of a said body a contrast medium according to claim 1 physiologically tolerable manganese compound and a physiologically tolerable reducing compound containing an α-hydroxy ketone group or salt thereof and generating a magnetic resonance image of the liver and abdomen of said body.

8. An MRI contrast agent kit comprising in a first container a physiologically tolerable manganese compound, and in a second container an uptake promoter comprising a physiologically tolerable reducing compound containing an α-hydroxy ketone group, or salt thereof, and wherein said manganese compound and uptake reducing compound are present in an amount sufficient to provide a molar ration of manganese compound and uptake promoter is from 1:0.2 to 1:50.

* * * * *

UNITED STATES PATENT AND TRADEMARK OFFICE
CERTIFICATE OF CORRECTION

PATENT NO. : 5,716,598

DATED : February 10, 1998

INVENTOR(S) : GOLMAN et al.

It is certified that error appears in the above-indentified patent and that said Letters Patent is hereby corrected as shown below:

Column 6, line 57, delete "200" and insert --300--.

Column 7, lines 8-11, delete the phrase "physiologically tolerable manganese . . . or salt thereof".

Column 8, line 4, delete "reducing compound" and insert --promoter--;

line 7, delete "ration" and insert --ratio--;

line 8, delete "is" and insert --of--.

Signed and Sealed this

Thirteenth Day of July, 1999

*Attest:*

Q. TODD DICKINSON

*Attesting Officer*     *Acting Commissioner of Patents and Trademarks*